United States Patent
Kraft et al.

(10) Patent No.: US 7,390,779 B2
(45) Date of Patent: Jun. 24, 2008

(54) CYCLOALKANECARBOXYLIC ACID DERIVATIVES AS FRAGANTS WITH MUSK CHARACTERISTICS

(75) Inventors: Philip Kraft, Dübendorf (CH); Riccardo Cadalbert, Zurich (CH)

(73) Assignee: Givaudan SA, Vernier (CH)

( * ) Notice: Subject to any disclaimer, the term of this patent is extended or adjusted under 35 U.S.C. 154(b) by 663 days.

(21) Appl. No.: 10/478,626

(22) PCT Filed: May 30, 2002

(86) PCT No.: PCT/CH02/00282

§ 371 (c)(1),
(2), (4) Date: Jun. 14, 2004

(87) PCT Pub. No.: WO02/096852

PCT Pub. Date: Dec. 5, 2002

(65) Prior Publication Data

US 2004/0234568 A1 Nov. 25, 2004

(30) Foreign Application Priority Data

Jun. 1, 2001 (EP) .................................. 01113377

(51) Int. Cl.
*A61K 8/18* (2006.01)
*A61Q 13/00* (2006.01)
*C07C 69/74* (2006.01)

(52) U.S. Cl. ............................ 512/8; 560/122; 560/123; 560/124

(58) Field of Classification Search .................. 424/405; 560/123, 124

See application file for complete search history.

(56) References Cited

U.S. PATENT DOCUMENTS 5,166,412 A    11/1992   Giersch et al. .............. 560/231

FOREIGN PATENT DOCUMENTS

| EP | 0 472 966 A1 | 3/1992 |
| EP | 0869 111 A1 | 10/1998 |
| WO | WO 00/14051 | 3/2000 |

OTHER PUBLICATIONS

PCT International Search Report for PCT/CH02/00282 dated Jul. 2, 2002.

*Primary Examiner*—Sreeni Padmanabhan
*Assistant Examiner*—Jody L Karol
(74) *Attorney, Agent, or Firm*—Norris McLaughlin & Marcus, PA

(57) ABSTRACT

Odourant compounds selected from compounds having the structure:

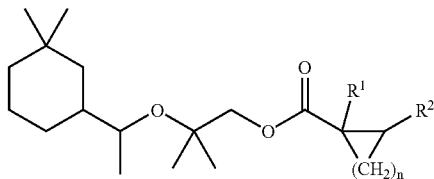

wherein,
$R^1$ and $R^2$ may be independently hydrogen or methyl, and n is an integer 1, 2 or 3 provided that n+ the carbon atoms in $R^1$ and $R^2$ is less than 5, their preparation and their use in fine fragrances and perfume components, wherein the compounds provide a musk characteristic.

12 Claims, No Drawings

CYCLOALKANECARBOXYLIC ACID DERIVATIVES AS FRAGANTS WITH MUSK CHARACTERISTICS

This application is filed as a 35 USC 371 application of PCT/CH02/00282.

The invention is concerned with new odourant compounds that have musk characteristics.

Conventional musks have been selected from polycyclic aromatics, nitro-arenes and certain macrocyclic molecules. However, in recent years there has been great activity to find novel compounds having musky characteristics to replace these conventional musks, the use of which is becoming more restricted because of, e.g. environmental concerns.

In recent years, research activity has resulted in the development of new families of compounds with musk characteristics. In DE 2513996, for example there is described a family of compounds exemplified by the product <<cyclomusk>>.

(1)

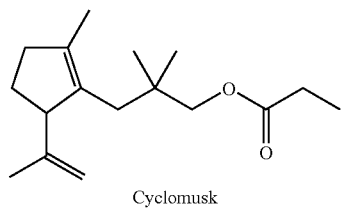

Cyclomusk

Cyclomusk is characterised as having very strong musky properties. Nevertheless, attempts were made to improve on the olfactory properties of cyclomusk and its related compounds. Thus, in EP 472966 the cyclopentenyl group characteristic of cyclomusk was replaced by 3,3-dimethylcyclopentyl and 3,3-dimethylcyclohexyl groups to give a new family of compounds (exemplified by (2) and (3) below) also displaying strong musk characteristics.

(2)

(3)

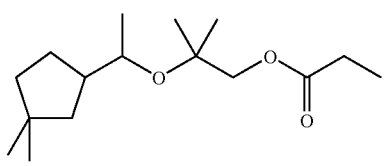

Helvetolide

In WO 00/14051, there are described further derivatives wherein the gem-dialkyl group on the chain characteristic of compound (3), is replaced by a carbonyl group. Compound (4), an example of such derivatives has been described as having a stronger musky smell than prior art molecules.

(4)

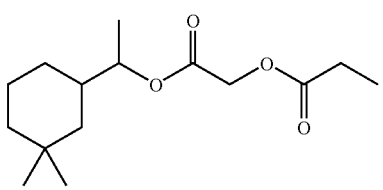

In the effort to develop alternatives to, or improve upon, conventional musks, e.g. macrocyclic musks, the focus has been therefore to produce molecules which may be described generally as 4-oxaoctan-3-ones that are 8,8-disubstituted with at least one bulky substituent (exemplified by compounds (1) through (4)), and to derivatise at either the bulky substituent at the left-hand side of the 2-D structures depicted, or to derivatise in the centre of the chain, for example by replacing gem-dimethyl functionality with a carbonyl group. Conspicuously, the right-hand end (as depicted in these 2D representations) of the prior art molecules are consistently only linear or branched alicyclic esters, and only the propionates have been shown to display musk notes sufficiently pronounced to compete with the commercial macrocyclic musks on the market.

The lack of derivatisation at this ester moiety is understandable based on the prior art teaching that for a molecule to have useful odourant properties the molecular weight thereof must not be so high as to reduce its vapour pressure to a point where it does not release its odour. In fact, the prior art teaches that the highest molecular weight known for an odourant molecule is 294 (see G. Ohloff, Scents and Fragrances, The Fascination of Odors and their Chemical Perspectives, Springer Verlag, Berlin, 1994, p. 9). Compounds (1) to (4) have molecular weights approaching this upper limit, viz. 264, 270, 284 and 270 respectively. The skilled person would therefore expect that further derivatisation at this ester moiety, that would have the effect of increasing the molecular weight of the molecule, would not result in a compound having useful odourant properties.

Surprisingly however, we have now found that compounds having the general structure of compound (3) hereinabove described wherein the propionate ester moiety is replaced with a certain cycloalkyl ester moiety have musk characteristics that make them suitable for use as odourant molecules in fragrances compositions.

Accordingly the invention provides in one of its aspects a compound of formula (I)

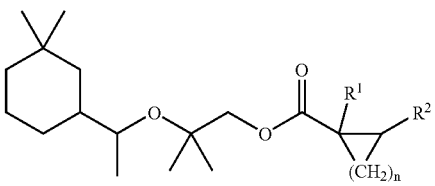

wherein,
$R^1$ and $R^2$ may be independently hydrogen or methyl, or $R^1$ and $R^2$ together may be $CH_2$, and
n is an integer 1, 2 or 3 provided that n+the carbon atoms in $R^1$ and $R^2$ is less than 5.

The compounds of formula (I) represent a small group of novel compounds that possess a musk note that may compete with the known macrocyclic musks and that are stronger, more distinct and better performing than the known propionates (1) through (4). These properties are surprising, not least, in that the compounds of the formula (I) have molecular weights in excess of the previously thought maximum molecular weight for odourant molecules.

Additional compounds were prepared (see compounds (11) and (12) below).

(11)

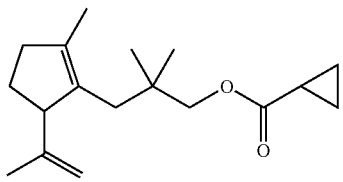

-continued

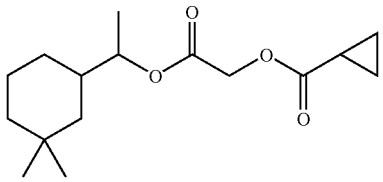

(12)

These compounds were tested for musky properties but were found to have only weak musk characteristics and not to exhibit the characteristics of the compounds of the formula (I). From all indications therefore, the cycloalkyl ester moiety is not alone, definitive with respect to the impressive musk characteristics of these compounds. Rather, it would appear that the impressive musk characteristics are a result of the interaction of the cycloalkyl group with the other specific functionality defining these compounds. The compounds of formula (I) therefore represent a small group of molecules with very specific functionality that give olfactive properties that are impressive and entirely unpredictable.

Preferred compounds of the formula (I) are represented by the general formula,

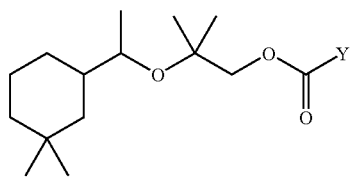

wherein, Y represents a cyclopropyl residue [compound (5)]; a 2-methylcyclopropyl residue [compound (6)]; a cyclobutyl residue [compound (7)]; a cyclopentyl residue [compound (8)]; a 1,2-dimethyl cyclopropyl residue [compound (9)]; and a 1-methylcyclopropyl residue [compound (10)].

The compounds of formula (I) comprise more than one chiral centre and as such they may exist as a mixture of enantiomers and diastereomers, or they may be resolved as enantiomerically and diastereomerically pure forms. However, resolving steroisomers adds to the complexity of manufacture and purification of these compounds and so it is preferred to use a compound of formula (I) as a mixture of its stereoisomers simply for economic reasons. However, if it is desired to prepare pure stereoisomers, this may be achieved according to methodology known in the art.

The compounds of formula (I) display impressive musk characteristics yet at the same time have diminished fruity aspects, which fruity aspects are characteristic of Helvetolide (3). Additionally, the compounds possess unique notes that make them useful also in signature accords. These signature notes add a certain character that may be described as aspects that are somewhat woody, liquorice and agrestic. However, these unique aspects do not detract from the broad range of possible applications in perfumery typical of musk odourants and the compounds may find use in practically all fields of perfumery, for example in fine perfumery, or in perfumed products of all kinds, for example luxury perfumes, cosmetic articles, consumer healthcare products or household products, e.g. washing agents, detergents and soaps.

In these applications the compounds of formula (I) may be used alone or in admixture with other fragrances. Preferably however, the compounds of the formula (I) are admixed with other fragrance molecules. The use of a compound of formula (I) in this regard is not limited to any particular perfume type nor to any special olfactory direction, odourant or class of substance. Thus, compounds of the formula (I) may be mixed with, for example, ethereal oils and extracts, e.g. castoreum, costus root oil, oak moss absolute, geranium oil, jasmin absolute, patchouli oil, rose oil, sandalwood oil or ylang-ylang oil;

alcohols, e.g. citronellol, EBANOL®, eugenol, geraniol, SUPER MUGUET®, linalool, phenylethyl alcohol, SANDALORE®, terpineol or TIMBEROL®;

aldehydes and ketones, e.g. α-amylcinnamialdehyde, GEORGYWOOD®, hydroxycitronellal, ISO H SUPER®, ISORALDEINE®, HEDIONE®, maltol, methyl cedryl ketone, methylionone or vanillin;

ether and acetals, e.g AMBROX®, geranyl methyl ether, rose oxide or SPIRAMBRENE®;

esters and lactones, e.g. benzyl acetate, cedryl acetate, Cyclomusk (1), γ-decalactone, HELVETOLIDE® (3), γ-undecalactone or vetivenyl acetate;

macrocycles, e.g. ambrettolide, ethylene brassylate or EXALTOLIDE®; and heterocycles, e.g. isobutylchinoline.

However, due to their unique character, the compounds of formula (I) are especially well suited for use as fresh musky accords in woody-spicy and floral-hesperidic compositions as is more specifically illustrated in the Examples.

EBANOL®, SUPER MUGUET®, SANDALORE®, TIMBEROL®; GEORGYWOOD®, ISO E SUPER®, ISORALDEINE®, HEDIONE®, AMBROX®, SPIRAMBRENE®, HELVETOLIDE® AND EXALTOLIDE®; are proprietary names of fragrancing compounds or fragrancing constituents available from their respective supplier.

In addition to their admixture with other fragrances, the compounds of formula (I) may be admixed with one or more ingredients or excipients conventionally used in conjunction with fragrances in fragrance compositions, for example carrier materials, and other auxiliary agents commonly used in the art.

The proportions in which the compounds of formula (I) are employed in compositions according to the present invention may vary within a large range of values and will depend upon the nature of the composition one intends to perfume, for example the nature of co-ingredients, and the particular effect that the perfumer seeks. Generally however, one may employ up to about 30% by weight in fine fragrances and up to about 50% by weight in other perfumed products.

The compounds of the formula (I) may be prepared by the esterification of the alcohol of the formula,

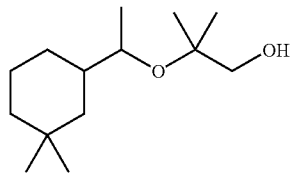

with the corresponding cycloalkyl carboxylic acid according to generally known synthetic procedures. Specific reaction conditions that may be employed are set forth in the examples, e.g. Example 2.

The alcohol starting material is known in the art, see for example EP 472 966, whereas the carboxylic acids are either generally known or may be prepared from commonly available starting materials according to generally known synthetic protocols.

There now follows a series of examples that serve to illustrate the invention. The NMR data are given relative to TMS standard.

EXAMPLE 1

2-[1'-(3",3"-Dimethylcyclohexyl)ethoxy]-2-methyl-propan-1-ol (Compound A)

At 0° C. under an atmosphere of nitrogen, 178 ml (321 mmol) of a 1.8 M solution of ethyl aluminium dichloride in toluene was slowly added to a stirred solution of 100 g (641 mmol) of 1-(3',3'-dimethylcyclohexyl)ethanol and 55.4 g (769 mmol) of isobutylenoxide in 500 ml of cyclohexane. After complete addition, the cooling bath was removed, the reaction mixture was allowed to warm to room temperature, and stirring was continued at this temperature for 15 h. The reaction mixture was then poured into 1 L of brine, acidified with concentrated phosphoric acid, and thrice extracted with ether. The combined organic extracts were washed with brine and water, dried with sodium sulphate, and concentrated on a rotary evaporator. Distillation of the crude material (136 g) provided at 78-85° C./0.3 mbar 55.1 g (38%) of pure 2-[1'-(3",3"-dimethylcyclohexyl)-ethoxy]-2-methylpropan-1-ol, while 60.4 g of starting material were recovered.

EXAMPLE 2

Cyclopropanecarboxylic acid 2'-[1"-(3'",3'"-dimethyl cyclohexyl)ethoxy]-2'-methylpropyl ester (5).

1.50 g (6.58 mmol) of the compound A and 0.56 g (6.58 mmol) of cyclopropanecarboxylic acid were dissolved in 20 ml of anhydrous dichloromethane under an atmosphere of nitrogen. At 0° C., a solution of 160 mg (1.31 mmol) of 4-(dimethylamino)pyridine in 20 ml of anhydrous dichloromethane was added with stirring, followed after further stirring for 5 minutes by a solution of 1.49 g (7.24 mmol) of N,N'-dicyclohexylcarbodiimide in 20 ml of anhydrous dichloromethane. After stirring for 1 h at 0°, the cooling bath was removed and the reaction mixture was stirred at room temperature for 15 h. The insoluble material was then filtered off by suction, and thoroughly washed with dichloromethane. The organic solutions were combined, and concentrated to dryness under reduced pressure. The crude material (2.75 g) was purified by flash chromatography (100 g silica gel, pentane/ether, 19:1, $R_f$=0.45) to furnish 1.46 g (75%) of the olfactory pure target compound cyclopropanecarboxylic acid 2'-[1"-(3'",3'"-dimethyl-cyclohexyl)ethoxy]-2'-methylpropyl ester (5).

Compound (5) had a strong, intense, musk odour, that was linear, but with some slight woody, liquorice-like nuances. IR (neat): ν=1163 cm$^{-1}$(ν C—C(=O)—O), 1072 (ν C—O—C—C), 1731 (ν OC=O). —$^1$H-NMR (CDCl$_3$): δ=0.70-1.66 (m, 14H, 2-H -6'''-H$_2$), 0.86/0.87/0.90/0.90 (s, 6H, 3'''-Me$_2$), 1.06 (d, J=6.2 Hz)/1.07 (d, J=6.2 Hz, 3H, 2"-H$_3$), 1.18 (4 s, 6H, 2'-Me$_2$), 3.37 (dq, J=6.2, 6.2 Hz, 1H, 1"-H), 3.90 (br. s)/3.92 (d, J=11.4 Hz)/3.94 (d, J=11.4 Hz, 2H, 1'-H$_2$).—$^{13}$C-NMR(CDCl$_3$): δ=8.20 (2t, C-2, C-3), 12.84 (d, C-1), 19.56/19.75 (q, C-2"), 22.15/22.16 (t, C-5'''), 23.60/23.65/23.98/24.02 (q, C-3',2'-Me), 24.52/24.59 (q, 3'''-Me axial), 28.16/29.22 (t, C-6'''), 30.51/30.52 (s, C-3'''), 33.52/33.56 (q, 3'''-Me equat.), 39.23/39.25 (t, C-2'''), 40.21/40.26 (d, C-1'''), 41.47/42.13 (t, C4'''), 70.16/70.25 (t, C-1'), 71.64/71.68 (d, C-1"), 73.60/73.67 (s, C-2'), 174.56/174.60 (s, COO). —MS (EI): m/z (%)=197 (3) [M$^+$-C$_5$H$_7$O$_2$], 185 (2) [C$_8$H$_{15}^+$], 141 (59) [C$_8$H$_{13}$O$_2^+$], 83 (29) [C$_6$H$_{11}^+$], 69 (100) [C$_5$H$_9^+$].

EXAMPLES 3 TO 6

2-Methylcyclopropanecarboxylic acid 2'-[1"-(3'",3'"-dimethylcyclohexyl)ethoxy]-2'-methylpropyl ester (6); cyclobutanecarboxylic acid 2"-[1"-(3'",3'"-dimethyl-cyclohexyl)ethoxy]-2'-methylpropyl ester (7); cyclopentanecarboxylic acid 2'-[1"-(3'",3'"-dimethyl-clyclohexyl)ethoxy]-2'-methylpropyl ester (8); and 1-methylcyclopropane carboxylic acid 2'-[1"-(3'",3'"-dimethylcyclohexyl)ethoxy]-2'-methylpropyl ester (10) were synthesised by reacting compound A, prepared according to Example 1, with the corresponding carboxylic acid in a procedure analogous to that of Example 2.

Compound (6) was a colourless liquid having a strong, intense, musk odour that was linear, but with some slight woody nuances, very close in odour to compound (5) of the previous example.—IR (neat): ν=1161 cm$^{-1}$(ν C—C(=O)—O), 1042/1074 (ν C—O—C—C), 1729 (ν OC=O).—$^1$H-NMR (CDCl$_3$): δ=0.70-1.73 (m, 13H, 2-H-6'''-H$_2$), 0.86/0.87/0.90/0.90 (s, 6H, 3'''-Me$_2$), 1.05 (d, J=6.0 Hz)/1.06 (d, J=6.4 Hz, 3H, 2"-H$_3$), 1.11 (d, J=5.6 Hz, 3H, 2-Me), 1.18 (4 s, 6H, 2'-Me$_2$), 3.37 (dq, J=6.0, 6.0 Hz, 1H, 1"-H), 3.91 (br. s)/3.92 (d, J=11.4 Hz)/3.94 (d, J=11.4 Hz, 2H, 1'-H$_2$).—$^{13}$C-NMR (CDCl$_3$): δ=16.59 (t, C-3), 17.02/1703 (d, C-2), 17.73 (q, 2-Me), 19.55/19.75 (q, C-2"), 21.20/21.24 (d, C-1), 22.15/22.17 (t, C-5'''), 23.60/23.65/24.02/24.06 (q, C-3', 2'-Me), 24.51/24.60 (q, 3'''-Me axial), 28.15/29.22 (t, C-6'''), 30.51/30.52 (s, C-3'''), 33.51/33.56 (q, 3'''-Me equat.), 39.24/39.26 (t, C-4'''), 40.20/40.27 (d, C-1'''), 41.47/42.13 (t, C-4'''), 70.16/70.21 (t, C-1'), 71.66/71.68 (d, C-1"), 73.65/73.66 (s, C-2'), 174.16/174.21 (s, COO).—MS (EI): m/z (%)=199 (1) [M$^+$-C$_8$H$_{15}$], 197 (3) [M$^+$-C$_6$H$_9$O$_2$], 155 (57) [C$_9$H$_{15}$O$_2^+$], 139 (49) [C$_{10}$H$_{19}^+$], 83 (100) [C$_5$H$_7$O$^+$], 55 (42) [C$_4$H$_9^+$].

Compound (7) was a colourless liquid with a strong, intense, musk odour that was linear, but with some slight woody nuances, very close in odour to compounds (5) and (6).—IR (neat): ν=1163 cm$^{-1}$(ν C—C(=O)—O), 1059 (ν C—O—C—C), 1734 (ν OC=O).—$^1$H-NMR (CDCl$_3$): ν=0.86/0.88/0.90/0.91 (s, 6H, 3'''-Me$_2$), 1.05 (d, J=6.0 Hz)/1.06 (d, J=6.0 Hz, 3H, 2"-H$_3$), 1.18 (4 s, 6H, 2'-Me$_2$), 1.20-1.71 (m, 9H, 1'''-H-6'''-H$_2$), 1.89-1.99 (m, 2H, 3-H$_2$), 2.18-2.33 (m, 4H, 2-,4-H$_2$), 3.38 (dq, J=6.0, 3.6 Hz, 1H, 1"-H), 3.93 (d, J=12.0 Hz)/3.94 (br. s)/3.96 (d, J=12.0 Hz, 2H, 1'-H$_2$).—$^{13}$C-NMR (CDCl$_3$): δ=18.32 (t, C-3), 19.58/19.80 (q, C-2"), 22.14/22.16 (t, C-5'''), 23.58/23.65/23.95/23.95 (q, C-3', 2'-Me), 24.51/24.59 (q, 3'''-Me axial), 25.12/25.13/25.15/25.15 (t, C-2,-4), 28.18/29.23 (t, C-6'''), 30.50/30.52 (s, C-3'''), 33.51/33.56 (q, 3'''-Me equat.), 38.09/38.12 (d, C-1), 39.23/39.25 (t, C-4'''), 40.21/40.29 (d, C-1'''), 41.53/42.07 (t, C-4'''), 70.06/70.15 (t, C-1'), 71.62/71.72 (d, C-1"), 73.66/72.72 (s, C-2'), 175.12/175.12 (s, COO).—MS (EI): m/z (%)=197 (4) [M$^+$-C$_6$H$_9$O$_2$], 155 (84) [C$_9$H$_{15}$O$_2^+$], 139 (67) [C$_{10}$H$_{19}^+$], 83 (97) [C$_5$H$_7$O$^+$], 69 (28) [C$_5$H$_9^+$], 55 (100) [C$_4$H$_9^+$].

Compound (8) was a colourless liquid having a strong, intense, musk odour that was linear, but with some slight agrestic nuances.—IR (neat): ν=1735 cm$^{-1}$ (ν OC=O), 1158 (ν C—C(=O)—O), 1043/1016 (ν C—O—C—C).—$^1$H-NMR (CDCl$_3$): δ=0.86/0.87/0.89/0.90 (s, 6H, 3'''-Me$_2$), 1.05 (d, J=6.4 Hz)/1.06 (d, J=6.4 Hz, 3H, 2"-H$_3$), 1.20/1.21 (4 s, 6H, 2'-Me$_2$), 1.31-1.60 (m, 9H, 1-H'''-6'''-H$_2$), 1.61-1.92 (m, 8H, 2-H$_2$-5-H$_2$), 2.77 (quint, J=7.6 Hz, 1H, 1-H), 3.37 (dq, J=6.4, 6.0 Hz, 1H, 1"-H), 3.92 (d, J=11.2 Hz)/3.94 (br. s)/3.95 (d, J=12.8 Hz, 2H, 1'-H$_2$).—$^{13}$C-NMR (CDCl$_3$): δ=19.58/

19.80 (q, C-2"), 22.14/22.15 (t, C-5'"), 23.60/23.70/23.95/23.96 (q, C-3', 2'-Me), 24.51/24.59 (q, 3'"-Me axial), 25.61 (4 t, C-3,-4), 28.18/29.21 (t, C-6'"), 29.78/29.81/29.83/29.84 (t, C-2,-5), 30.50/30.52 (s, C-3'"), 33.51/33.55 (q, 3'"-Me equat.), 39.23/39.25 (t, C-4'"), 40.22/40.29 (d, C-1'"), 41.53/42.06 (t, C-4"'), 43.86/43.87 (d, C-1), 70.11/70.18 (t, C-1'), 71.59/71.69 (d, C-1"), 73.66/73.71 (s, C-2'), 176.35/176.38 (s, COO).—MS (EI): m/z (%)=197 (5) [M$^+$-C$_7$H$_{11}$O$_2$], 169 (86) [C$_{10}$H$_{17}$O$_2{}^+$], 139 (81) [C$_{10}$H$_{19}{}^+$], 123 (9) [C$_9$H$_{15}{}^+$], 97 (80) [C$_6$H$_9$O$^+$], 83 (50) [C$_5$H$_7$O$^+$], 69 (100) [C$_5$H$_9{}^+$], 55 (40) [C$_4$H$_9{}^+$].

Compound (10) was an colourless liquid with an odour that was musky, linear, but weaker than that of compounds (5) through (8).—IR (neat): ν=1158 cm$^{-1}$(ν C—C(=O)—O), 1725 (ν OC=O), 1044 (ν C—O—C—C).—$^1$H-NMR (CDCl$_3$): δ=0.68 (m$_c$, 2H, 2-H$_2$), 0.70-1.66 (m, 11H, 3-H$_2$-6'"-H$_2$), 0.86/0.87/0.90/0.90 (s, 6H, 3'"-Me$_2$), 1.05 (d, J=6.4 Hz)/1.06 (d, J=6.4 Hz, 3H, 2"-H$_3$), 1.17 (4 s, 6H, 2'-Me$_2$), 1.31/1.32 (s, 3H, 1-Me), 3.37 (dq, J=6.4, 6.0 Hz, 1H, 1"-H), 3.88 (d, J=11.2 Hz)/3.90 (br. s)/3.92 (d, J=11.2 Hz, 2H, 1'-H$_2$).—$^{13}$C-NMR (CDCl$_3$): δ=16.59/16.61 (t, C-2, C-3), 18.41 (2 s, C-1), 19.24 (2q, 1-Me), 19.57/19.76 (q, C-2"), 22.11/22.13 (t, C-5'"), 23.44/23.63/23.95/24.07 (q, C-3', 2'-Me), 24.49/24.59 (q, 3'"-Me axial), 28.14/29.11 (t, C-6'"), 30.49/30.51 (s, C-3'"), 33.50/33.54 (q, 3'"-Me equat.), 39.23/39.26 (t, C-4'"), 40.17/40.28 (d, C-1'"), 41.48/42.03 (t, C-4'"), 70.33/70.46 (t, C-1'), 71.56/71.62 (d, C-1"), 73.60/73.67 (s, C-2'), 175.57/175.58 (s, COO).—MS (EI): m/z (%)=210 (1) [M$^+$-C$_5$H$_8$O$_2$], 197 (3) [M$^+$-C$_6$H$_9$O$_2$], 155 (75) [C$_9$H$_{15}$O$_2{}^+$], 139 (52) [C$_{10}$H$_{19}{}^+$], 83 (100) [C$_5$H$_7$O$^+$], 55 (46) [C$_4$H$_9{}^+$].

EXAMPLE 7

Tiglic acid 2'-[1"-(3'",3'"-dimethylcyclohexyl)ethoxy]-2'-methylpropyl ester (Compound B)

In analogy to the preparation of Compound (5), 10.0 g (43.8 mmol) of Compound A and 4.38 g (43.8 mmol) of tiglic acid were esterified in anhydrous dichloromethane in the presence of 530 mg (4.38 mmol) of 4-(dimethylamino)pyridine and 9.94 g (48.2 mmol) of N,N'-dicyclohexylcarbodiimide. The usual work-up provided 17.9 g of crude product, which was purified by flash chromatography (400 g silica gel, pentane/ether, 19:1, R$_f$=0.36) to furnish 9.44 g (69%) of pure tiglic acid 2'-[1"-(3'",3'"-dimethylcyclohexyl)ethoxy]-2'-methylpropyl ester, of which 3.10 g (10.0 mmol) were used in the subsequent reaction.

EXAMPLE 8

1,2-Dimethylcyclopropanecarboxylic acid 2'-[1"-(3'",3'"-dimethylcyclohexyl)ethoxy]-2'-methylpropyl ester (9).

With stirring, 10 mg (0.06 mmol) of silver acetate was dissolved in 10 ml of hot concentrated acetic acid. 1.70 g (26 mmol) of zinc dust was added in one dash, and stirring was continued for 1 minute. The heating source was removed and the reaction allowed to cool down to room temperature. The formed zinc-silver couple was isolated by decanting, and washed with 10 ml of concentrated acetic acid and five times with 10 ml of ether. Then 15 ml of anhydrous ether was poured on the product and a small batch of silver wool was added, followed by 3.10 g (10 mmol) of Compound B. During 5 minutes 3.48 g (13 mmol) of diiodomethane was added drop wise with stirring to this ethereal suspension, and the reaction was heated to reflux for two days, with supplementary addition of 3.48 g (13 mmol) of diiodomethane after one day. After cooling down to room temperature, the reaction mixture was poured into 200 ml of an icy cold saturated aqueous ammonium chloride solution. The product was extracted twice with 100 ml of ether, and the combined ethereal extracts were washed with 50 ml of water, 50 ml of 40% aqueous sodium hydrogen sulphite, again two times with 50 ml of water, and finally with 25 ml of brine. The combined extracts were then dried with sodium sulphate, concentrated on a rotary evaporator, and taken up in 10 ml hexane. At room temperature, with stirring, bromine was added drop wise, until the solution remained brownish. The solution was then poured onto ice and extracted twice with 50 ml of ether. The ethereal extracts were combined, washed with 50 ml of saturated aqueous sodium hydrogen carbonate, 50 ml of water and 25 ml of brine, and dried with sodium sulphate. Evaporation of the solvent furnished 3.46 g of crude material, which was purified by flash chromatography (120 g silica gel, pentane/ether, 19:1, R$_f$=0.42) to provide 720 mg (22%) of the olfactory pure target compound 1,2-dimethyl cyclopropanecarboxylic acid 2'-[1"-(3'",3'"-dimethylcyclohexyl)ethoxy]-2'-methylpropyl ester (9).

Compound (9) was a colourless liquid with a musky odour that was linear, but weaker than compounds (5) through (8).—IR (neat): ν=1157 cm$^{-1}$(ν C—C(=O)—O), 1721 (ν OC=O), 1095/1071 (ν C—O—C—C).—$^1$H-NMR (CDCl$_3$): δ=0.34 (m$_c$, 1H, 3-H$_a$), 0.70-1.70 (m, 11H, 3-H$_b$-6'"-H$_2$), 0.86/0.87/0.90/0.90 (s, 6H, 3'"-Me$_2$), 1.05 (d, J=6.0 Hz)/1.06 (d, J=6.4 Hz, 3H, 2"-H$_3$), 1.11 (d, J=6.0 Hz)/1.12 (d, J=6.4 Hz, 3H, 2-Me), 1.17 (4 s, 6H, 2'-Me$_2$), 1.27/1.28 (s, 3H, 1-Me), 3.36/3.37 (2dq, J=6.0, 6.0 Hz, 1H, 1"-H), 3.88 (d, J=11.0 Hz)/3.88 (d, J=2.0 Hz)/3.91 (d, J=11.0 Hz, 2H, 1'-H$_2$).—$^{13}$C-NMR (CDCl$_3$): δ=13.25/13.57 (4q, 1-,2-Me), 19.59/19.77 (q, C-2"), 21.17/21.19 (d, C-2), 22.13/22.15 (t, C-5'"), 22.39 (2 s, c-1), 23.44/24.00/24.04/24.15 (q, C-3', 2'-Me), 23.62 (2 t, C-3), 24.49/24.59 (q, 3'"-Me axial), 28.16/29.16 (t, C-6'"), 30.51/30.53 (s, C-3'"), 33.51/33.54 (q, 3'"-Me equat.), 39.25/39.27 (t, C-4'"), 40.17/40.28 (d, C-1'"), 41.50/42.06 (t, C-4'"), 70.34/70.46 (t, C-1'), 71.57/71.64 (d, C-1"), 73.63/73.70 (s, C-2'), 176.04/176.07 (s, COO).—MS (EI): m/z (%)=197 (6) [M$^+$-C$_7$H$_{11}$O$_2$], 169 (92)[C$_{10}$H$_{17}$O$_2{}^+$], 139 (87) [C$_{10}$H$_{19}{}^+$], 114 (8) [C$_6$H$_{10}$O$_2{}^+$], 97 (100) [C$_6$H$_9$O$^+$], 69 (61) [C$_5$H$_{11}{}^+$].

EXAMPLE 9

Cyclopropanecarboxylic acid 3'-(5"-isopropenyl-2"-methyl cyclopent-1-enyl)-2',2'-dimethylpropyl ester (11)

In analogy to the preparation of compounds (5) and (6), 0.70 g (3.37 mmol) of 3-(5-isopropenyl-2-methylcyclopent-1-enyl)-2,2-dimethylproanol, prepared according to Hoffmann and von Fraunberg (DE 2513996, Example 3), and 0.28 g (3.37 mmol) of cyclopropanecarboxylic acid were esterified in anhydrous dichloromethane in the presence of 410 mg (3.37 mmol) of 4-(dimethylamino)pyridine and 760 mg (3.37 mmol) of N,N'-dicyclohexylcarbodiimide. The usual work-up provided 1.59 g of crude product, which was purified by flash chromatography (100 g silica gel, pentane/ether, 49:1, R$_f$=0.50) to provide 0.87 g (94%) of the targeted cyclopropanecarboxylic acid 3-(5-isopropenyl-2-methyl-cyclopent-1-enyl)-2,2-dimethyl-propyl ester (11).

Compound (11) had a weak fruity-musky raspberry-type odour.—IR (neat): ν=1172 cm$^{-1}$(ν C—C(=O)—O), 1730 (ν OC=O), 889 (ν C=C—H oop), 1073 (ν C—O—C—C).—$^1$H-NMR (CDCl$_3$): δ=0.85 (m$_c$, 2H, 2-,3-H$_a$), 0.91 (s, 6H, 2'-Me$_2$), 1.00 (m$_c$, 2H, 2-,3-H$_b$), 1.54 (s, 3H, 2"-CH$_3$), 1.59-1.65 (m, 2H, 4"-H$_2$), 1.66 (s, 3H, 2'"-H$_3$), 1.75 (d, J=13.6 Hz, 1H, 3'-H$_b$), 1.97 (m$_c$, 1H, 1-H), 2.12 (d, J=13.6 Hz, 1H, 3'-H$_a$), 2.28 (t, J=7.0 Hz, 2H, 3"-H$_2$), 3.31 (m$_c$, 1H, 5"-H), 3.75 (s, 2H, 1'-H$_2$), 4.45 (dt, J=2.8, 0.4 Hz, 1H, trans 1'''=CH$_2$), 4.70 (dq, J=2.8, 1.2 Hz, 1H, cis 1'''=CH$_2$).—$^{13}$C-NMR (CDCl$_3$): δ=8.04/8.07 (t, C-2,-3), 12.85 (d, C-1), 14.86 (q, 2''-Me), 18.57 (q, 2'''-H$_3$), 24.90/25.11 (q, 2'-Me$_2$), 27.70 (t, C-4''), 34.57 (t, C-3''), 36.18 (s, C-2'), 37.29 (t, C-3'), 57.81 (d, C-5''), 72.43 (t, C-1'), 110.58 (t, 1'''=CH$_2$), 133.30 (s, C-2''), 137.14 (s, C-1''), 148.34 (s, C-1'''), 174.79 (s, COO).—MS (EI): m/z (%)=276 (14) [M$^+$], 207 (2) [M$^+$-C$_4$H$_5$O], 190 (3) [M$^+$-C$_4$H$_6$O$_2$], 175 (36) [M$^+$-C$_5$H$_9$O$_2$], 161 (16)/147 (36)/133 (16)/119 (45)/105 (31)/91 (37)/77 (22) [C$_n$H$_{2n-7}^+$], 121 (30) [C$_9$H$_{13}^+$], 69 (100) [C$_4$H$_5$O$^+$].

EXAMPLE 10

Cyclopropanecarboxylic acid 1''-(3''',3'''-dimethyl cyclohexyl)ethoxycarbonylmethyl ester (12)

Following our general procedure, 15.6 g (100 mmol) of 1-(3',3'-dimethylcyclohexyl)ethanol were esterified with 9.45 g (100 mmol) of chloroacetic acid in anhydrous dichloromethane in the presence of 1.22 g (10 mmol) of 4-(dimethylamino)pyridine and 22.7 g (110 mmol) of N,N'-dicyclohexylcarbodiimide. The usual work-up provided 28.4 g of crude product, which was purified by flash chromatography (600 g silica gel, pentane/ether, 19:1, R$_f$=0.77) to provide 20.5 g (88%) of chloroacetic acid 1-(3,3-dimethylcyclohexyl) ethyl ester, 4.80 g (20.6 mmol) of which were dissolved in 50 ml of diethyl ketone and 13 ml of 1,4-dioxane. To this solution, 1.77 g (20.6 mmol) of cyclopropanecarboxylic acid and 5.69 g (41.2 mmol) of potassium carbonate were added, and the resulting mixture was refluxed for 20 h. The reaction mixture was then poured onto 100 g of ice, and the product was extracted twice with 150 ml of ether. The combined ethereal extracts were washed with 100 ml of water and 50 ml of brine, dried with sodium sulphate, and concentrated under reduced pressure to furnish 26.0 g of crude material. This was purified by flash chromatography (175 g silica gel, pentane/ether, 9:1, R$_f$=0.52) to provide 3.56 g (61%) of the target compound cyclopropanecarboxylic acid 1-(3,3-dimethylcyclohexyl)ethoxycarbonylmethyl ester (12).

Compound (12) had a weak floral-musky, rosy odour.—IR (neat): ν=1159 cm$^{-1}$ (ν C—C(=O)—O), 1737 (ν OC=O), 1101 (ν C—O—C—C).—$^1$H-NMR (CDCl$_3$): δ=0.81-1.72 (m, 13H, 1-H-6'''-H$_2$), 0.87/0.88/0.91/0.91 (s, 6H, 3'''-Me$_2$), 1.19 (d, J=6.4 Hz, 3H, 2'''-H$_3$), 1.74 (m$_c$, 1H, 1'''-H), 4.59/4.60 (s, 2H, 2'-H$_2$), 4.77/4.78 (dq, J=6.4, 1.4 Hz, 1H, 1''-H).—$^{13}$C-NMR (CDCl$_3$): δ=8.65/8.68 (t, C-2,-3), 12.46 (2 d, C-1), 16.82/16.96 (2q, C-2''), 21.66/21.74 (t, C-5'''), 24.39/24.48 (q, 3'''-Me axial), 27.86/28.11 (t, C-6'''), 30.34/30.41 (S, C-3'''), 33.32 (2q, 3'''-Me equat.), 38.10/38.23 (d, C-1'''), 38.87/38.89 (t, C-2'''), 40.87/41.33 (t, C-4'''), 60.71 (2 d, C-1''), 76.11/76.20 (t, C-2'), 167.49 (2 s, 1'-COO), 174.01/174.02 (s, 1-COO).—MS (EI): m/z (%)=138 (22) [C$_{10}$H$_{18}^+$], 127 (30) [C$_6$H$_7$O$_3^+$], 123 (44) [C$_9$H$_{15}^+$], 83 (33) [C$_6$H$_{11}^+$], 69 (100) [C$_5$H$_9^+$].

EXAMPLE 11

Musky-woody, Spicy-fresh Fine Fragrance

| compound/ingredient | parts by weight 1/1000 |
|---|---|
| 1. Amberketal @ 10% in IPM (isopropyl myristate) | 20 |
| 2. Ambrettolide | 6 |
| 3. Amyl salicylate | 7 |

-continued

| compound/ingredient | parts by weight 1/1000 |
|---|---|
| 4. BHT (butyl hydroxy toluene) @ 10% in DPG (dipropylene glycol) | 5 |
| 5. Calone 1951 (7-methyl-3,4-dihydo-2H-1,5-benzodioxepin-3-one) @ 10% in DPG | 3 |
| 6. cardamom oil pure | 2 |
| 7. Cashmeran (1,2,3,5,6,7-hexahydro-1,1,2,3,3-pentamethyl-4H-inden-4-one) | 1 |
| 8. Citrus essence oil, colourless, citroptene free | 35 |
| 9. citronellol, laevorotatory @ 10% in DPG | 3 |
| 10. Cyclohexal (4-(4-hydroxy-4-methylpentyl)-cyclohex-3-en-1-carboxaldehyde) | 50 |
| 11. dimethyl phenylethyl carbinol (2-methyl-4-phenylbutan-2-ol) @ 10% in DPG | 2 |
| 12. ethyl linalool (3,7-dimethylnona-1,6-dien-3-ol) | 70 |
| 13. ethylene brassylate | 200 |
| 14. "Fruit Vert GR3" perfumery base (Givaudan) | 8 |
| 15. Galaxolide 50 PHT | 150 |
| 16. "Galbex 183 E" perfumery base (Firmenich) | 5 |
| 17. guaiac wood oil | 8 |
| 18. Habanolide (oxacyclohexadec-12/13-en-2-one) | 20 |
| 19. Hedione HC (cis-methyl (3-oxo-2-pentyl-cyclopentyl)acetate | 7 |
| 20. hydroxycitronellal, synthetic | 7 |
| 21. IPM (isopypyl myristate) | 100 |
| 22. Iso E Super (1-(1,2,3,4,5,6,7,8-octahydro-2,3,8,8-tetramethyl-2-naphthalenyl)ethanone) | 95 |
| 23. isoeugenol @ 1% in DPG | 5 |
| 24. lavender oil, French, "orpur" | 7 |
| 25. linalool, synthetic | 10 |
| 26. linalyl acetate | 20 |
| 27. mandarin oil, Italian, "orpur" | 5 |
| 28. Muscenone (3-methylcyclopentadec-4/5-enone) | 10 |
| 29. nutmeg oil | 7 |
| 30. pyralone @ 10% in DPG | 2 |
| 31. Thibetolide (pentadecan-15-olide) | 80 |
| 32. Tropional (alpha-methyl-1,3-benzo-dioxole-5-propanal) | 10 |
| 33. Compound (5) | 40 |
|  | 1000 |

Compound (5) conveys to this musky-woody, spicy-fresh fine fragrance its freshness and its unique musky character. Where the same amounts of Helvetolide (3) or ethylene brassylate are very low key on top, compound (5) brings lift and a very bright freshness while still being sensual. Furthermore, compound (5) increases the substantivity significantly, much more than Helvetolide (3) does at the same dosage. The pronounced fruity side note of Helvetolide (3) leads also to disharmonies that are not observed in the original formula with compound (5).

EXAMPLE 12

Fresh, Floral-hesperidic Vanilla Perfume for Shower Gel

| compound/ingredient | parts by weight 1/800 |
|---|---|
| 1. alpha-hexyl cinnamaldehyde | 210 |
| 2. benzaldehyde @ 10% in DPG | 1 |
| 3. benzyl acetate, extra quality | 35 |
| 4. benzylic alcohol, extra quality | 5 |
| 5. beta-ionone | 9 |
| 6. cinnamaldehyde | 2 |

-continued

| | compound/ingredient | parts by weight 1/800 |
|---|---|---|
| 7. | cis-3-dodecenal (mandarin aldehyde) @ 10% in DPG | 5 |
| 8. | coumarin, pure, crystalline | 10 |
| 9. | dipropylene glycol (DPG) | 123 |
| 10. | 8-ethyl-1-oxaspiro[4.5]decan-2-one (Ethyl laitone) @ 1% in TEC | 5 |
| 11. | ethyl maltol @ 1% in DPG | 8 |
| 12. | ethyl vanillin | 5 |
| 13. | eugenol, pure | 2 |
| 14. | geraniol | 50 |
| 15. | Geranitrile T (3,7-dimethyl-2,6-octadiene-nitrile) | 2 |
| 16. | geranyl acetate, synthetic | 5 |
| 17. | hydroxycitronellal, synthetic | 10 |
| 18. | lauric aldehyde @ 10% in DPG | 5 |
| 19. | Lemarome N | 3 |
| 20. | linalool, synthetic | 50 |
| 21. | linalyl acetate, synthetic | 60 |
| 22. | Prunolide (gamma-nonalactone) | 20 |
| 23. | Sandalore (5-(2,2,3-trimethylcyclopent-3-en-1-yl)-3-methylpentan-2-ol) | 60 |
| 24. | terpineol, pure | 5 |
| 25. | Tricyclal (2,4-dimethylcyclohex-3-ene-1-carbaldehyde) | 3 |
| 26. | vanillin | 2 |
| 27. | Yara Yara (2-methoxynaphthalene) @ 10% in DPG | 5 |
| 28. | Compound (5) | 100 |
| | | 800 |

Compound (5) conveys to this fresh, floral-hesperidic vanilla perfume a pleasant, sensual and comfortable musk note without making it appeal heavy or old fashioned. It brings elegance and crispness into the olfactory picture and underlines the functional caring character of the product. In comparison with equal amounts of Helvetolide (3), the composition incorporating compound (5) is more sensual and velvety, the one with Helvetolide (3) more fruity, which leads to a certain disharmony. Compound (5), however, does blend very well with the sweet vanilla note, made up of coumarin, vanillin and ethyl maltol, as well as with the floral facets brought by geraniol, linalool, hydroxycitronellal and alpha-hexylcinnam aldehyde. In comparison with Helvetolide (3) the hesperidic elements are also enhanced with compound (5).

The invention claimed is:

1. A compound selected from formula (I)

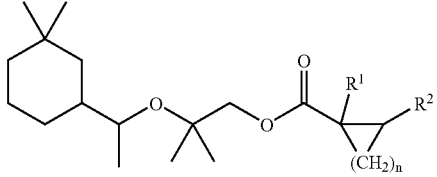

wherein, $R^1$ and $R^2$ may be independently hydrogen or methyl, and n is an integer 1, 2 or 3 provided that n+ the carbon atoms in $R^1$ and $R^2$ is less than 5.

2. A compound according to claim 1 wherein n=1, selected from substituted and unsubstituted cyclopropanoates.

3. A compound according to claim 1, wherein n=2 or 3, selected from cyclobutanoates and cyclopentanoates.

4. A compound according to claim 1 selected from the group consisting of:

cyclopropanecarboxylic acid 2'-[1"-(3'",3'"-dimethyl-cyclohexyl)ethoxy]-2'-methylpropyl ester, 2-methylcyclopropanecarboxylic acid 2'-[1"-(3'",3'"-dimethylcyclohexyl)ethoxy]-2'-methylpropyl ester, cyclobutanecarboxylic acid 2'-[1"-(3'",3'"-dimethylcyclohexyl)ethoxy]-2'-methylpropyl ester, cyclopentanecarboxylic acid 2'-[1"-(3'",3'"-dimethyl-cyclohexyl)ethoxy]-2'-methylpropyl ester, 1,2-dimethylcyclo-propanecarboxylic acid 2'-[1"-(3'",3'"-dimethylcyclohexyl)ethoxy]-2'-methylpropyl ester, and 1-methylcyclopropanecarboxylic acid 2'-[1"-(3'",3'"-dimethylcyclohexyl)ethoxy]-2'-methylpropyl ester.

5. A fragrance composition comprising at least one compound according to claim 1.

6. A method of imparting a musk odor to a fragrance composition, comprising the step of:

providing at least one compound according to claim 1 to the fragrance composition.

7. A fragrance composition comprising at least one compound according to claim 2.

8. A fragrance composition comprising at least one compound according to claim 3.

9. A fragrance composition comprising at least one compound according to claim 4.

10. A method of imparting a musk odor to a fragrance composition, comprising the step of:

providing at least one compound according to claim 2 to the fragrance composition.

11. A method of imparting a musk odor to a fragrance composition, comprising the step of:

providing at least one compound according to claim 3 to the fragrance composition.

12. A method of imparting a musk odor to a fragrance composition, comprising the step of:

providing at least one compound according to claim 4 to the fragrance composition.

* * * * *